United States Patent [19]

Watanabe et al.

[11] 4,361,653

[45] Nov. 30, 1982

[54] PLASMINOGEN PREPARATIONS

[75] Inventors: Ryozo Watanabe, Takatsuki; Mitsuomi Ohgaki, Fukuchiyama, both of Japan

[73] Assignee: The Green Cross Corporation, Osaka, Japan

[21] Appl. No.: 225,532

[22] Filed: Jan. 16, 1981

[30] Foreign Application Priority Data

Jul. 3, 1980 [JP] Japan .................................. 55/91341

[51] Int. Cl.³ .......................... C12N 9/96; C12N 9/68
[52] U.S. Cl. ................................................ 435/188
[58] Field of Search ........................ 435/217, 188, 212

[56] References Cited

U.S. PATENT DOCUMENTS

| | | | |
|---|---|---|---|
| 3,227,626 | 1/1966 | Baumgarten et al. | 435/217 |
| 3,340,156 | 9/1967 | Jensen | 435/217 |
| 3,732,146 | 5/1973 | Heimburger | 435/217 |
| 3,865,692 | 2/1975 | Holleman | 435/217 |

OTHER PUBLICATIONS

Methods in Enzymology, vol. 19, pp. 184–199 (1970).

*Primary Examiner*—Lionel M. Shapiro
*Attorney, Agent, or Firm*—Cushman, Darby & Cushman

[57] ABSTRACT

A plasminogen preparation comprising a plasminogen-containing aqueous solution or of plasminogen dry powder each admixed with at least one of lysine, phenylmethanesulfonyl fluoride, aprotinin, and soybean trypsin inhibitor in an effective amount for stabilizing plasminogen.

5 Claims, No Drawings

PLASMINOGEN PREPARATIONS

The present invention relates to a preparation of plasminogen originated from warm-blooded animals including humankind and to a method for stabilization thereof. More particularly, it relates to a plasminogen preparation characterized by being admixed with a plasmin inhibitor in an effective amount for stabilizing plasminogen and to a method for stabilizing a plasminogen preparation characterized by adding thereto a plasmin inhibitor in an effective amount for stabilizing plasminogen.

Plasminogen is activated by urokinase or the like and converted to plasmin, which decomposes fibrin into soluble matter, i.e., causes fibrinolysis. Plasminogen is used for studies on fibrinolysis, and in addition, for clinical applications as a fibrinolytic, therapeutic agent (for treatment thrombosis) in recent years.

Plasminogen itself is a stable enzyme precursor, but practically all preparations of plasminogen contain small amounts of plasmin, which causes during storage the activation of plasminogen into plasmin, and moreover, plasminogen turns into plasmin also by self-digestion. Hence, plasminogen is unstable in the form of preparation. Thus, the present inventors conducted extensive studies, and as a result, found that various kinds of plasmin inhibitors improve the stability of plaminogen when added to preparations thereof, whereby the present invention has been accomplished.

An object of this invention is to provide a method for stabilizing plasminogen which comprises adding a plasmin inhibitor in an effective amount for said stabilization to an aqueous solution containing plasminogen or to plasminogen dry powder.

Another object of this invention is to provide a stabilized plasminogen preparation.

Other objects and advantages of this invention will be apparent from the following description.

The plasmin inhibitors used in this invention include lysine, phenylmethanesulfonyl fluoride, aprotinin, and soybeam trypsin inhibitor. These inhibitors can be used each alone or in combination thereof.

The plasminogen-containing aqueous solution used in this invention is not particularly limited. It includes those obtainable by various known purification methods from the plasminogen-containing fractions, such as fraction III of Cohn's low temperature alcohol fractionation in the blood plasma protein fractionation generally applied to the production of important biological medicines such as blood serum, blood plasma and ascites of human and animals, and further, such as fibrinogen, γ-globulin, and albumin in the blood plasma. The dry powder of plasminogen includes the dry powder from the above aqueous solutions containing plasminogen, particularly the lyophilized powder thereof.

As typical examples of methods for purifying crude plasminogen, there are methods by use of a fixed plasmin inhibitor [Japanese Patent application Kokai (laid-open) No. 153,592/1980) ] and by use of lysine-Sepharose [Science, 170, 1095 (1970)].

While the effective amount of the plasmin inhibitor to be added depends upon the amount of plasmin in the plasminogen preparation and the kind of the inhibitors, the stabilizing effect of the inhibitor increases with amount thereof in the case of lysine. However, said amount should be adjusted according to the purpose of using the plasminogen preparation. For instance, for the purpose of studies on fibrinolysis, the concentration of the inhibitor in desirably less than the lowest value effecting fibrinolysis. Further, in case of the purpose of pharmaceutical applications where plasminogen preparations undergo a severe treatment, for example, heat treatment at 60° C. for 10 hours to inactivate viruses, a large amount of the inhibitor is added, and after a severe treatment of the preparation, it is removed by dialysis or some other suitable methods. In the cases of PMSF (phenylmethanesulfonyl fluoride; the same applies hereinafter), aprotinin, and soybean trypsin inhibitor, it is important to add an enough amount of inhibitor to inhibit contaminating plasmin completely.

Specific concentration of the inhibitors used in this invention are as follows:

For aqueous solutions of plasminogen, lysine is used to give a final concentration of 0.001 to 5 W/V%, PMSF 0.01 to 100 mM, aprotinin 0.1 to 1,000 KIU/ml, and soybean trypsin inhibitor 1 to 1,000 BAEEU/ml. For dry power of plasminogen, lysin is used to give a final concentration of 0.01 to 10 W/W %, PMSF 0.01 to 10 W/W %, aprotinin 0.01 to 1,000 KIU/mg, and soybean trypsin inhibitor 0.1 to 1,000 BAEEU/mg.

This invention will be illustrated in more detail by the following examples, but the invention is not limited thereto. In the Examples, an activity of plasminogen is shown by the casein unit (CU unit) [Vox Sang., 5, 357-376 (1960)], an activity of Aprotinin is shown by the KIU [Frey, E. K. Kraut, H. Werle, E (1950)Kallikrein (Padutil) Enke Verlaz, Stuttgart], and an activity of soybean trypsin inhibitor is shown by the BAEEU [Laskowski, M. (1955) Method in Enzymology 2, 37 Ed. by Colowick, S. P. and Kaplan, N. O. New York: Academic Press, Inc.].

EXAMPLE 1

(Stabilizing Effect on Plasminogen Solution)

Various kinds of inhibitors were each added to an aqueous solution of 100 CU/ml plasminogen in Tris-HCl buffer (pH 7.8). The solutions were allowed to stand in a thermostat of 37° C. to test the stabilities. The results are shown in Table 1.

TABLE 1

| Inhibitor | Final concentration | Remaining activity on standing at 37° C. for 24 hours (%) |
|---|---|---|
| Lysine | 0.1% | 95 |
| " | 1.0% | 96 |
| PMSF | 0.1 mM | 98 |
| " | 1 mM | 98 |
| Aprotinin | 1 KIU/ml | 89 |
| " | 10 KIU/ml | 95 |
| Soybean trypsin inhibitor | 10 BAEEU/ml | 88 |
| Soybean trypsin inhibitor | 100 BAEEU/ml | 92 |
| No additive | — | 43 |

EXAMPLE 2

(Stabilizing Effect on Lyophilized Plasminogen)

The solutions of Example 1, to which various kinds of inhibitor had been added, were lyophilized, and the resulting lyophilizates were allowed to stand for 1 month in a thermostat of 50° C. or for 3 months at room temperature to test the stabilities. The results are shown in Table 2.

TABLE 2

| Inhibitor | Remaining activity on standing at 50° C. for 1 month (%) | Remaining activity after 3-month storage at room temperature (%) |
| --- | --- | --- |
| Lysine | 97 | 96 |
| PMSF | 94 | 93 |
| Aprotinin | 91 | 90 |
| Soybean trypsin inhibitor | 93 | 91 |
| No additive | 32 | 25 |

What is claimed is:

1. A plasminogen containing at least one member selected from the group consisting of phenylmethanesulfonyl fluoride, aprotinin, and soybean trypsin inhibitor in an effective amount for stabilizing plasminogen.

2. A method for producing a plasminogen preparation which comprises adding at least one member selected from the group consisting of phenylmethanesulfonyl floride, aprotinin, and soybean trypsin inhibitor in an effective amount for stabilizing plasminogen, to an aqueous solution containing plasminogen, and lyophilizing the resulting solution.

3. A plasminogen preparation according to claim 1, wherein the preparation is in the form of dry powder, and contains aprotinin in an amount of 0.01 to 1,000 KIU/mg.

4. A plasminogen preparation according to claim 1, wherein the preparation is in the form of dry powder and contains soybean trypsin inhibitor in an amount of 0.1 to 1,000 BAEEU/mg.

5. A plasminogen preparation according to claim 1, wherein the preparation is in the form of dry powder, and contains phenylmethane sulfonyl fluoride in an amount of 0.01 to 10 w/w %.

* * * * *